(12) United States Patent
Callen et al.

(10) Patent No.: US 7,049,101 B1
(45) Date of Patent: May 23, 2006

(54) ENZYMES HAVING HIGH TEMPERATURE POLYMERASE ACTIVITY AND METHODS OF USE THEREOF

(75) Inventors: Walter Callen, San Diego, CA (US); Eric J. Mathur, Carlsbad, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 09/656,309

(22) Filed: Sep. 6, 2000

Related U.S. Application Data

(60) Continuation-in-part of application No. 09/391,340, filed on Sep. 7, 1999, now Pat. No. 6,492,511, which is a division of application No. 08/907,166, filed on Aug. 6, 1997, now Pat. No. 5,948,666.

(51) Int. Cl.
*C12P 19/34* (2006.01)
*C12N 9/12* (2006.01)

(52) U.S. Cl. .................. 435/91.1; 435/194; 435/6; 536/23.1; 536/23.2

(58) Field of Classification Search .............. 435/6, 435/194, 4, 183, 440, 462, 91.1, 91.2; 536/23.1, 536/23.2, 23.5, 23.7
See application file for complete search history.

(56) References Cited

U.S. PATENT DOCUMENTS

| | | | |
|---|---|---|---|
| 4,165,188 A | 8/1979 | Rempel ............... 400/248 |
| 4,683,195 A | 7/1987 | Mullis et al. ............ 435/6 |
| 4,683,202 A | 7/1987 | Mullis .................. 435/91 |
| 5,491,086 A * | 2/1996 | Gelfand et al. ......... 435/194 |
| H1531 H | 5/1996 | Blumentals et al. ...... 435/194 |
| 5,795,763 A | 8/1998 | Dahlberg et al. |
| 5,939,250 A * | 8/1999 | Short ................... 435/4 |
| 6,008,025 A | 12/1999 | Komatsubara et al. ... 435/91.2 |
| 6,077,664 A | 6/2000 | Slater et al. ............ 435/6 |
| 6,492,511 B1 | 12/2002 | Callen et al. |

FOREIGN PATENT DOCUMENTS

| | | |
|---|---|---|
| EP | 455430 | 4/1991 |
| EP | 0624641 | 11/1994 |
| JP | 07298879 | 11/1995 |
| JP | 07327684 | 12/1995 |
| WO | WO 99/07837 | 2/1999 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Stetter et al., Hyperthermophillic microorganisms FEMS Microbiology Reviews 75:117-124.
Pley et al., *Pyrodictium abyssi* sp. nov. Represents a Novel Heterotrotropphic Marine Archael Hyperthermophile Growing at 110 °C, 1991, Systematic and Applied Microbiology, 14:245-255.
Pearson et al., "Improved tools for biological sequence comparison", Prc. Natl Acad. Sci USA, vol. 85, pp. 2444-2448, Apr. 1988 Biochemistry.
Madigan et al. *Scientific American*, "Extremophiles", Apr. 1997, pp. 82-87.
Choi, et al., "Purification and properties of *Thermus filiformis* DNA polymerase expressed in *Escherichia coli*", Biotechnol. Appl. Biochem., vol. 30, pp. 19-25, 1999.
Deckert et al., Nature 392:353-358 (1998).
Edgell et al., Journal of Bacteriology 179:2632-2640 (1997).
Supplementary European Search Report mailed on Jul. 6, 2004, for European patent application No. EP 98940988, filed on Aug. 6, 1998, 4 pages.
Pisani et al., Nucleic Acids Research 20(11):2711-2716 (1992).
Uemori, et al., "The hyperthermophilic archaeon Pyrodictium occultum has two alpha-like DNA polymerases", *J. Bacteriology*, vol. 177, No. 8, pp. 2164-2177, 1995.
Campbell, et al., "General properties and applications of monoclonal antibodies", Elsevier Science Publishers, section 1.1. pp. 1-32, 1984.

(Continued)

*Primary Examiner*—Richard Hutson
(74) *Attorney, Agent, or Firm*—Morrison & Foerster LLP

(57) ABSTRACT

The invention relates to thermostable polymerases that have polymerase activity temperatures in the range from 90° C. up to 113° C., such as those derived from *Pyrolobus fumaria*, and to polynucleotides encoding the polymerases In addition, methods of designing new thermostable DNA polymerases and methods of use thereof are also provided. The polymerases have increased activity and stability at increased pH and temperature.

1 Claim, 9 Drawing Sheets

OTHER PUBLICATIONS

Bost, et al., "Antibodies Against a Peptide Sequence Within the HIV Envelope Protein Crossreacts with Human Interleukin-2", *Immunological Investigations*, vol. 17, No. 6 & 7, pp. 577-586, 1988.

Bendayan, "Possibilities of False Immunocytochemical Results Generated by the Use of Monoclonal Antibodies: The Example of the Anti-proinsulin Antibody", *The Journal of Histochemistry and Cytochemistry*, vol. 43, No. 9, pp. 881-886, 1995.

Colman, "Effects of amino acid sequence changes on antibody-antigen interactions" *Research in Immunology*, vol. 145, No. 1, pp. 33-36.

Lederman, et al., "A single Amino Acid Substitution in a Common African Allele of the CD4 Molecule Ablates Binding of the Monoclonal Antibody, OKT4", *Molecular Immunology*, vol. 28, No. 11, pp. 1171-1181, 1991.

Abaza, et al., "Effects of Amino Acid Substitutions Outside an Antigenic Site on Protein Binding to Monoclonal Antibodies of predetermined Specificity Obtained by Peptide Immunization: Demonstration with Region 94-100 (Antigenic Site 3) of Myoglobin", *Journal of Protein Chemistry*, vol. 11, No. 5, pp. 433-444.

Ngo, et al., "Computational Complexity, Protein Structure Prediction and the Levinthal Paradox", *The Protein Folding Problem*, Ch. 14, pp. 491-494.

* cited by examiner

*Pyrolobus fumarius* DNA Polymerase (1PY2)

(SEQ ID NO:1) ATG ACT GAA GTT GTA TTC ACG GTT TTA GAC TCT AGC TAC GAG GTT GTT GGT
(SEQ ID NO:2) Met Thr Glu Val Val Phe Thr Val Leu Asp Ser Ser Tyr Glu Val Val Gly

AAA GAG CCT CAG GTA ATC ATA TGG GGT ATT GCT GAG AAC GGC GAG AGG GTA
Lys Glu Pro Gln Val Ile Ile Trp Gly Ile Ala Glu Asn Gly Glu Arg Val

GTC CTC ATT GAC AGG TCT TTT CGC CCA TAC TTC TAT GCG CTG CTT GCA CCG
Val Leu Ile Asp Arg Ser Phe Arg Pro Tyr Phe Tyr Ala Leu Leu Ala Pro

GGC GCC GAT CCT AAG CAG GTA GCA CAA CGT ATT CGT GCA TTG AGT AGG CCA
Gly Ala Asp Pro Lys Gln Val Ala Gln Arg Ile Arg Ala Leu Ser Arg Pro

AAG AGC CCG ATT ATA GGT GTA GAG GAT GAC AAG AGG AAG TAC TTC GGG AGG
Lys Ser Pro Ile Ile Gly Val Glu Asp Asp Lys Arg Lys Tyr Phe Gly Arg

CCT CGT AGG GTC TTA CGT ATT CGC ACC GTG CTA CCC GAG GCT GTT AGG GAG
Pro Arg Arg Val Leu Arg Ile Arg Thr Val Leu Pro Glu Ala Val Arg Glu

TAT CGC GAA CTC GTA AAG AAC GTT GAT GGT GTT GAG GAT GTT CTA GAG GCG
Tyr Arg Glu Leu Val Lys Asn Val Asp Gly Val Glu Asp Val Leu Glu Ala

GAT ATA CGC TTC GCT ATG CGC TAT CTC ATA GAT CAC GAT CTA TTT CCT TTC
Asp Ile Arg Phe Ala Met Arg Tyr Leu Ile Asp His Asp Leu Phe Pro Phe

ACC TGG TAC CGT GTA GAG GCT GAG CCC CTC GAG AAC AAG ATG GGC TTC CGT
Thr Trp Tyr Arg Val Glu Ala Glu Pro Leu Glu Asn Lys Met Gly Phe Arg

GTC GAC AAG GTA TAC CTG GTT AAG AGC AGG CCG GAG CCA CTT TAT GGT GAG
Val Asp Lys Val Tyr Leu Val Lys Ser Arg Pro Glu Pro Leu Tyr Gly Glu

FIGURE 1-A

```
GCT CTC GCA CCA ACC AAG CTT CCC GAT CTT AGG ATA CTC GCG TTC GAT ATT
Ala Leu Ala Pro Thr Lys Leu Pro Asp Leu Arg Ile Leu Ala Phe Asp Ile

GAA GTT TAT AGC AAG CAA GGG TCG CCG CGT CCA GAG CGC GAT CCT GTA ATA
Glu Val Tyr Ser Lys Gln Gly Ser Pro Arg Pro Glu Arg Asp Pro Val Ile

GTG ATA GCT GTG AAG ACT GAC GAT GGC GAT GAG GTG CTA TTC ATT GCA GAG
Val Ile Ala Val Lys Thr Asp Asp Gly Asp Glu Val Leu Phe Ile Ala Glu

GGC AAA GAC GAT CGA AAA CCG ATA CGC GAG TTT GTA GAG TAC GTG AAG AGG
Gly Lys Asp Asp Arg Lys Pro Ile Arg Glu Phe Val Glu Tyr Val Lys Arg

TAT GAC CCC GAC ATA ATA GTC GGT TAT AAC AAC AAT CAT TTC GAT TGG CCT
Tyr Asp Pro Asp Ile Ile Val Gly Tyr Asn Asn Asn His Phe Asp Trp Pro

TAT CTT TTG AGG CGC GCC CGC ATC CTA GGC ATA AAG CTT GAT GTG ACT AGA
Tyr Leu Leu Arg Arg Ala Arg Ile Leu Gly Ile Lys Leu Asp Val Thr Arg

AGA GTT GGC GCC GAG CCC ACC ACT AGC GTA CAT GGG CAC GTC TCT GTC CCT
Arg Val Gly Ala Glu Pro Thr Thr Ser Val His Gly His Val Ser Val Pro

GGC AGG CTT AAC GTA GAT CTG TAC GAC TAT GCC GAA GAG ATG CCA GAG ATC
Gly Arg Leu Asn Val Asp Leu Tyr Asp Tyr Ala Glu Glu Met Pro Glu Ile

AAG ATA AAG AGT CTC GAG GAG GTC GCA GAG TAT CTA GGC GTG ATG AAG AAG
Lys Ile Lys Ser Leu Glu Glu Val Ala Glu Tyr Leu Gly Val Met Lys Lys

AGT GAA CGC GTT ATC ATC AAT TGG TGG GAG ATT CCA GAC TAT TGG GAC GAC
Ser Glu Arg Val Ile Ile Asn Trp Trp Glu Ile Pro Asp Tyr Trp Asp Asp

CCG AAG AAG AGA CCA CTA TTA CTG CAA TAC GCG CGC GAC GAT GTC CGC GCT
Pro Lys Lys Arg Pro Leu Leu Leu Gln Tyr Ala Arg Asp Asp Val Arg Ala

ACT TAC GGC TTA GCC GAG AAG ATA TTG CCG TTT GCT ATC CAG TTG TCG TAC
```

FIGURE 1-B

Thr Tyr Gly Leu Ala Glu Lys Ile Leu Pro Phe Ala Ile Gln Leu Ser Tyr

GTA ACA GGT CTC CCA CTA GAC CAG GTA GGT GCG ATG AGT GTT GGC TTT CGA
Val Thr Gly Leu Pro Leu Asp Gln Val Gly Ala Met Ser Val Gly Phe Arg

CTT GAA TGG TAC CTG ATA CGC GCG GCG TTT AAG ATG AAA GAG CTT GTG CCG
Leu Glu Trp Tyr Leu Ile Arg Ala Ala Phe Lys Met Lys Glu Leu Val Pro

AAC CGC GTT GAG CGC CCA GAA GAG ACT TAC CGT GGC GCT ATA GTT CTT GAG
Asn Arg Val Glu Arg Pro Glu Glu Thr Tyr Arg Gly Ala Ile Val Leu Glu

CCG TTG AGA GGC GTG CAC GAG AAT ATA GCC GTA CTC GAC TTT AGC TCG ATG
Pro Leu Arg Gly Val His Glu Asn Ile Ala Val Leu Asp Phe Ser Ser Met

TAC CCA AAC ATC ATG ATA AAG TAC AAT GTT GGT CCT GAC ACG CTT GTG AGG
Tyr Pro Asn Ile Met Ile Lys Tyr Asn Val Gly Pro Asp Thr Leu Val Arg

CCT GGT GAA AAG TGT GGC GAG TGT GGT TGC TGG GAG GCC CCG GAG GTC AAG
Pro Gly Glu Lys Cys Gly Glu Cys Gly Cys Trp Glu Ala Pro Glu Val Lys

CAC AGG TTC CGT AGG TGT CCG CCC GGC TTC TTC AAG ACA GTT CTT GAG AGG
His Arg Phe Arg Arg Cys Pro Pro Gly Phe Phe Lys Thr Val Leu Glu Arg

CTG TTA GAG CTT CGT AAG CGT GTG CGT GCT GAA ATG AAG AAG TAT CCT CCG
Leu Leu Glu Leu Arg Lys Arg Val Arg Ala Glu Met Lys Lys Tyr Pro Pro

GAT AGC CCA GAA TAT CGA CTG TTG GAT GAA AGG CAG AAG GCG TTG AAG GTT
Asp Ser Pro Glu Tyr Arg Leu Leu Asp Glu Arg Gln Lys Ala Leu Lys Val

CTT GCA AAC GCT AGT TAC GGC TAC ATG GGT TGG AGC GGC GCT AGG TGG TAT
Leu Ala Asn Ala Ser Tyr Gly Tyr Met Gly Trp Ser Gly Ala Arg Trp Tyr

TGC AGG GAG TGC GCA AAG GCT GTC ACG GCT TGG GGT AGG CAC CTC ATA CGC
Cys Arg Glu Cys Ala Lys Ala Val Thr Ala Trp Gly Arg His Leu Ile Arg

FIGURE 1-C

```
ACC GCC ATC AAC ATA GCT CGT AAA CTA GGC CTC AAG GTG ATC TAC GGT GAC
Thr Ala Ile Asn Ile Ala Arg Lys Leu Gly Leu Lys Val Ile Tyr Gly Asp

ACA GAT TCG CTC TTC GTG ACC TAT GAT CCG GAG AAG GTG GAA AAT TTC ATC
Thr Asp Ser Leu Phe Val Thr Tyr Asp Pro Glu Lys Val Glu Asn Phe Ile

AAA ATT ATA AAG GAG GAG CTG GGG TTC GAA ATC AAG CTA GAG AAG GTG TAC
Lys Ile Ile Lys Glu Glu Leu Gly Phe Glu Ile Lys Leu Glu Lys Val Tyr

AAA CGC TTA TTC TTT ACA GAG GCT AAG AAG AGG TAC GCT GGC CTT CTC GAG
Lys Arg Leu Phe Phe Thr Glu Ala Lys Lys Arg Tyr Ala Gly Leu Leu Glu

GAC GGA CGT ATA GAT ATT GTC GGT TTC GAG GCT GTA CGT GGC GAT TGG TGT
Asp Gly Arg Ile Asp Ile Val Gly Phe Glu Ala Val Arg Gly Asp Trp Cys

GAA CTC GCC AAG GAG GTT CAG ACT AAG GTT GTC GAA ATA GTA TTG AAG ACG
Glu Leu Ala Lys Glu Val Gln Thr Lys Val Val Glu Ile Val Leu Lys Thr

AGT GAG GTG AAC AAG GCT GTA GAG TAC GTC AGG AAG ATT GTG AAA GAG TTG
Ser Glu Val Asn Lys Ala Val Glu Tyr Val Arg Lys Ile Val Lys Glu Leu

GAG GAG GGC AAG GTT CCC ATA GAG AAG CTT GTA ATC TGG AAG ACC CTT AGT
Glu Glu Gly Lys Val Pro Ile Glu Lys Leu Val Ile Trp Lys Thr Leu Ser

AAG CGT CTT GAG GAG TAC ACA ACG GAG GCA CCA CAC GTC GTT GCA GCG AAG
Lys Arg Leu Glu Glu Tyr Thr Thr Glu Ala Pro His Val Val Ala Ala Lys

AGG ATG CTG TCA GCA GGC TAC CGG GTA AGC CCA GGC GAC AAG ATA GGG TAT
Arg Met Leu Ser Ala Gly Tyr Arg Val Ser Pro Gly Asp Lys Ile Gly Tyr

GTA ATA GTG AAG GGT GGT GGC CGT ATC AGT CAA AGA GCA TGG CCA TAC TTC
Val Ile Val Lys Gly Gly Gly Arg Ile Ser Gln Arg Ala Trp Pro Tyr Phe
```

FIGURE 1-D

```
ATG GTC AAG GAT CCT AGC CAG ATA GAC GTG ACC TAC TAT GTT GAC CAC CAA
Met Val Lys Asp Pro Ser Gln Ile Asp Val Thr Tyr Tyr Val Asp His Gln

ATC ATC CCG GCT GCA TTG AGA ATA CTG GGC TAC TTT GGC ATC ACC GAG AAG
Ile Ile Pro Ala Ala Leu Arg Ile Leu Gly Tyr Phe Gly Ile Thr Glu Lys

AAG CTG AAA GCA AGT GCA ACT GGG CAG AAG ACT CTC TTC GAC TTT CTA GCC
Lys Leu Lys Ala Ser Ala Thr Gly Gln Lys Thr Leu Phe Asp Phe Leu Ala
                2412
AAG AAG AGC AAG TAA
Lys Lys Ser Lys End
```

FIGURE 1-E

ENZYMES HAVING HIGH TEMPERATURE POLYMERASE ACTIVITY AND METHODS OF USE THEREOF

RELATED APPLICATIONS

This application is a Continuation-in-Part application of U.S. patent application Ser. No. 09/391,340, filed Sep. 7, 1999, issued as U.S. Pat. No. 6,492,511, Dec. 10, 2002, which is a divisional of U.S. patent application Ser. No. 08/907,166, filed Aug. 6, 1997, now issued as U.S. Pat. No. 5,948,666.

FIELD OF THE INVENTION

This invention relates generally to enzymes, polynucleotides encoding the enzymes, the use of such polynucleotides and polypeptides, and more specifically to enzymes having high temperature polymerase activity.

BACKGROUND

Thermophilic bacteria have received considerable attention as sources of highly active and thermostable enzymes. Interest in DNA polymerases from thermophilic microbes increased with the invention of nucleic acid amplification processes. The use of thermostable enzymes, such as those described in U.S. Pat. No. 4,165,188, to amplify existing nucleic acid sequences in amounts that are large compared to the amount initially present was described U.S. Pat. Nos. 4,683,195 and 4,683,202, which describe the PCR process. These patents are incorporated herein by reference.

The PCR process involves denaturation of a target nucleic acid, hybridization of primers, and synthesis of complementary strands catalyzed by a DNA polymerase. The amplification product of each primer becomes a template for the production of the desired nucleic acid sequence. If the polymerase employed is a thermostable enzyme, polymerase need not be added after every denaturation step, because heat will not destroy the polymerase activity. Thermostable DNA polymerases are not irreversibly inactivated even when heated to 93° C. to 95° C. for brief periods of time, as, for example, in the practice of DNA amplification by PCR. In contrast, at this elevated temperature *E. coli* DNA Pol I is inactivated.

Archaeal hyperthermophiles, such as *Pyrodictium* and *Methanopyrus* species, grow at temperatures up to about 110° C. and are unable to grow below 80 degree. C. (see, Stetter et al., 1990, FEMS Microbiology Reviews 75:1170124, which is incorporated herein by reference). These sulfur reducing, strict anaerobes are isolated from submarine environments. For example, *P. abyssi* was isolated from a deep sea active "smoker" chimney off Guaymas Mexico at 2,000 meters depth and in 320° C. of venting water (Pley et al., 1991, Systematic and Applied Microbiology 14:245). The hyperthermophile that lives at the highest known temperature, *Pyrolobus fumaria*, grows in the walls of hydrothermal vents, sometimes called smokers, through which superheated, mineral-rich fluids erupt. *Pyrolobus fumaria* reproduces best in an environment of about 105° C. and can multiply in temperatures of up to 113° C., but stops growing at temperatures below 90° C.

The more common thermophilic microorganisms have an optimum growth temperature at or about 90° C. and a maximum growth temperature at or about 100° C. These less extreme hyperthermophiles can be grown in culture. For example, a gene encoding DNA polymerase has been cloned and sequenced from *Thermococcus litoralis* (EP No. 455, 430). However, culture of the extreme hyperthermophilic microorganisms is made difficult by their inability to grow on agar solidified media. For example, individual cells of the *Pyrodictium* species are extremely fragile, and the organisms grow as fibrous networks, clogging the steel parts of conventional fermentation apparatus. Thus, standard bacterial fermentation techniques are extremely difficult for culturing *Pyrodictium*. (See Staley, J. T. et al. eds., Bergey's Manual of Systematic Bacteriology, 1989, Williams and Wilkins, Baltimore, which is incorporated herein by reference.) These and other difficulties may preclude laboratory culture for preparing large amounts of purified nucleic acid polymerase enzymes for characterization and amino acid sequence analysis.

There is a desire in the art to produce thermostable DNA polymerases having enhanced thermostability that may be used to improve the PCR process and to improve the results obtained when using a thermostable DNA polymerase in other recombinant techniques such as DNA sequencing, nick-translation, and reverse transcription. Accordingly, there is a need in the art for the characterization, amino acid sequence, DNA sequence, and expression in a non-native host, of hyperthermophile DNA polymerase that are stable at extreme high temperature to eliminate the difficulties associated with the native host.

SUMMARY OF THE INVENTION

The present invention meets these and other needs by providing an isolated nucleic acid having a sequence as set forth in SEQ ID NO: 1 and variants thereof having at least 70% sequence identity to SEQ ID NO: 1 and encoding polypeptides having polymerase activity at extreme high temperature, such as temperatures of 95° C. to 113° C., for four or more hours.

One aspect of the invention is an isolated nucleic acid having a sequence as set forth in SEQ ID NO: 1, sequences substantially identical thereto, and sequences complementary thereto.

Another aspect of the invention is an isolated nucleic acid including at least 10 consecutive bases of a sequence as set forth in SEQ ID NO: 1, sequences substantially identical thereto, and the sequences complementary thereto.

In yet another aspect, the invention provides an isolated nucleic acid encoding a polypeptide having a sequence as set forth in SEQ ID NO: 2 and variants thereof having at least 70% sequence identity to such sequences and encoding a polypeptide having thermostable polymerase activity at a temperature in a range from about 95° C. to 113° C.

Another aspect of the invention is an isolated nucleic acid encoding a polypeptide or a functional fragment thereof having a sequence as set forth in SEQ ID NO:2 and sequences substantially identical thereto.

Another aspect of the invention is an isolated nucleic acid encoding a polypeptide having at least 10 consecutive amino acids of a sequence as set forth in SEQ ID NO: 2, and sequences substantially identical thereto.

In yet another aspect, the invention provides a purified polypeptide having a sequence as set forth in SEQ ID NO: 2, and sequences substantially identical thereto.

Another aspect of the invention is an isolated or purified antibody that specifically binds to a polypeptide having a sequence as set forth in SEQ ID NO: 2, and sequences substantially identical thereto.

Another aspect of the invention is an isolated or purified antibody or binding fragment thereof, which specifically binds to a polypeptide having at least 10 consecutive amino acids of one of the polypeptides of SEQ ID NO: 2, and sequences substantially identical thereto.

Another aspect of the invention is a method of making a polypeptide having a sequence as set forth in SEQ ID NO: 2, and sequences substantially identical thereto. The method includes introducing a nucleic acid encoding the polypeptide into a host cell, wherein the nucleic acid is operably linked to a promoter, and culturing the host cell under conditions that allow expression of the nucleic acid.

Another aspect of the invention is a method of making a polypeptide having at least 10 amino acids of a sequence as set forth in SEQ ID NO: 2, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide.

Another aspect of the invention is a method of generating a variant including obtaining a nucleic acid having a sequence as set forth in SEQ ID NO: 1, sequences substantially identical thereto, sequences complementary to the sequences of SEQ ID NO: 1, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in SEQ ID NO: 1, and sequences substantially identical thereto, or a polypeptide sequence as set forth in SEQ ID NO: 2, and sequences substantially identical thereto.

Another aspect of the invention is a computer system including a processor and a data storage device wherein the data storage device has stored thereon a sequence as set forth in SEQ ID NO: 1, and sequences substantially identical thereto, or a polypeptide having a sequence as set forth in SEQ ID NO: 2, and sequences substantially identical thereto.

Another aspect of the invention is a method for comparing a first sequence to a reference sequence wherein the first sequence is a nucleic acid having a sequence as set forth in SEQ ID NO: 1, and sequences substantially identical thereto, or a polypeptide code of SEQ ID NO: 2, and sequences substantially identical thereto. The method includes reading the first sequence and the reference sequence through use of a computer program which compares sequences; and determining differences between the first sequence and the reference sequence with the computer program.

Another aspect of the invention is a method for identifying a feature in a sequence as set forth in SEQ ID NO: 1, and sequences substantially identical thereto, or a polypeptide having a sequence as set forth in SEQ ID NO: 2, and sequences substantially identical thereto, including reading the sequence through the use of a computer program which identifies features in sequences; and identifying features in the sequence with the computer program.

Another aspect of the invention is an assay for identifying fragments or variants of SEQ ID NO: 2, and sequences substantially identical thereto, which retain the extreme high temperature polymerase activity of the polypeptides of SEQ ID NO: 2 (i.e., at temperatures of 95° C. to 113° C., for four or more hours. The assay includes utilizing a polypeptide encoded by a nucleic acid having at least 70% homology to SEQ ID NO: 1, and sequences substantially identical thereto, or polypeptide fragment or variant encoded by SEQ ID NO: 1, to effect DNA polymerase activity in a PCR amplification at extreme high temperature for four or more hours and under conditions that allow said polypeptide or fragment or variant to function, and detecting formation of an amplification product, wherein formation of the amplification product is indicative of a functional DNA polymerase polypeptide or fragment or variant.

BRIEF DESCRIPTION OF THE DRAWINGS

The following drawings are illustrative of embodiments of the invention and are not meant to limit the scope of the invention as encompassed by the claims.

FIGS. 1A through 1E show the nucleotide and deduced amino acid sequence of DNA polymerase (1PY2) from *Pyrolobus fumaria*

DETAILED DESCRIPTION OF THE INVENTION

Figure 2:
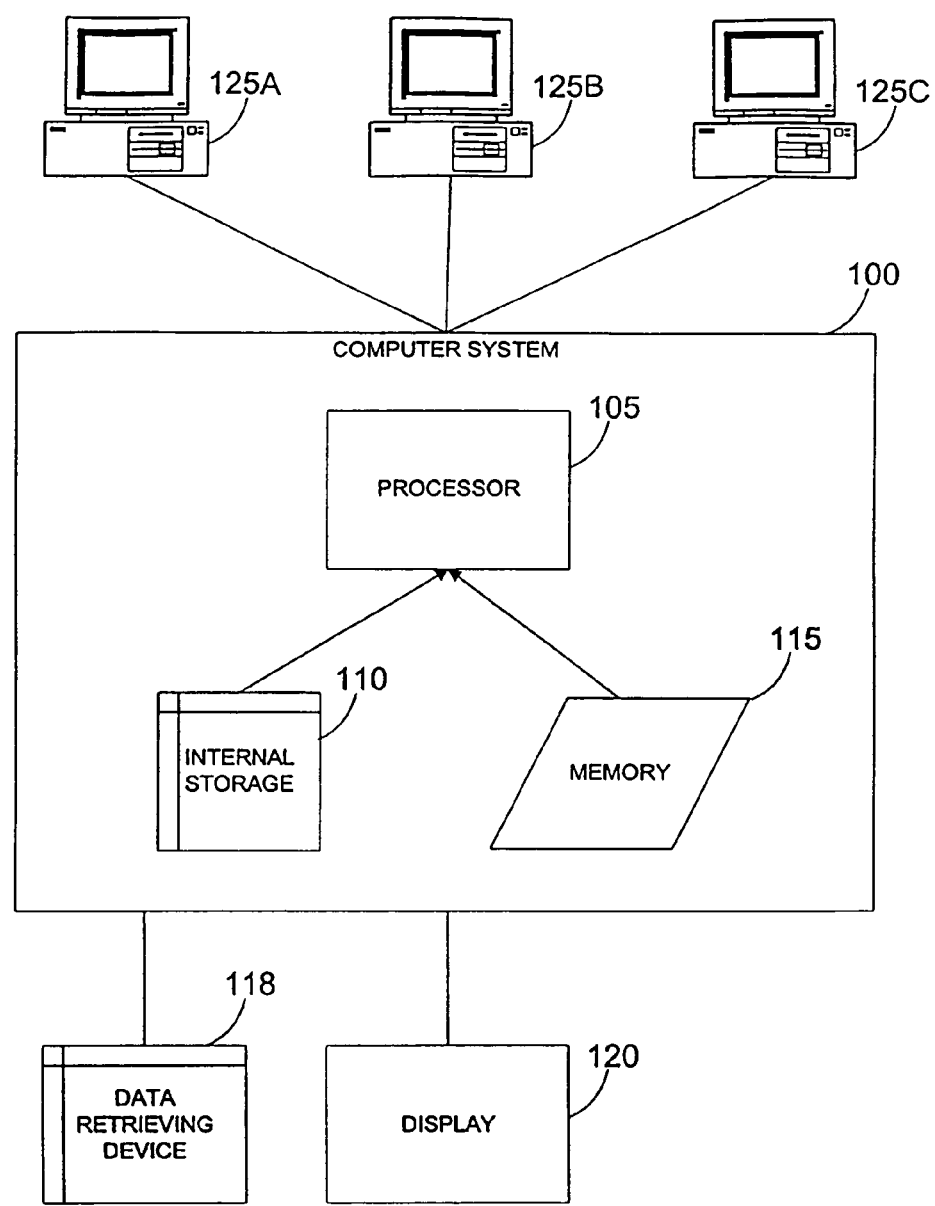
FIG. 2 is a block diagram of a computer system.

The present invention relates to DNA polymerases and polynucleotides encoding them. The polynucleotide encoding SEQ ID NO: 1 was originally recovered from a genomic gene library derived from *Pyrolobus fumaria*. This 2412 base pair polynucleotide encodes a protein having a deduced 803 amino acid sequence (SEQ ID NO:2).

The present invention provides purified thermostable DNA polymerases that catalyze DNA synthesis by addition of deoxynucleotides to the 3' end of a polynucleotide chain, using a complementary polynucleotide strand as a template. An exemplary purified enzyme is a polymerase derived from an organism referred herein as "*Pyrolobus fumaria*," a hyperthermophile that grows in the walls of hydrothermal vents through which superheated, mineral-rich fluids erupt. *Pyrolobus fumaria* reproduces best in an environment of about 105° C. and can multiply in temperatures of up to 113° C., but stops growing at temperatures below 90° C. This exemplary enzyme (shown in FIG. 1B) may be used to polymerize DNA where desired. The polymerase enzyme of the present invention has a very high thermostability and processivity. The *Pyrolobus fumaria* polymerase remains robustly active even after four or more hours at temperatures as high as 95° C. to 113° C. Therefore it is particularly useful and reliable for PCR amplification of template molecules greater than 20 kb in length and/or having a GC content of greater than 90%, templates which typically require longer amplification times and higher temperatures.

One property found in the *Pyrolobus fumaria* DNA polymerase enzymes, but lacking in native Taq DNA polymerase and native Tth DNA polymerase, is 3'→5' exonuclease activity. This 3'→5' exonuclease activity, which is commonly known as a "proof-reading" activity, is generally considered to be desirable because misincorporated or unmatched bases of the synthesized nucleic acid sequence are eliminated by this activity. Therefore, the fidelity of PCR utilizing a polymerase with 3'→5' exonuclease activity (e.g. the invention *Pyrolobus fumaria* DNA polymerase enzymes) is increased. However, the 3'→5' exonuclease activity found in DNA polymerase enzymes can also increase non-specific background amplification in PCR by modifying the 3' end of the primers. The 3'→5' exonuclease activity can eliminate single-stranded DNAs, such as primers or single-stranded template. In essence, every 3'-nucleotide of a single-stranded primer or template is treated by the enzyme as unmatched and is therefore degraded. To avoid primer degradation in PCR, one can add phosphorothioate to the 3' ends of the primers. Phosphorothioate modified nucleotides are more resistant to removal by 3'→5' exonucleases.

Whether one desires to produce an enzyme identical to native *Pyrolobus fumaria* DNA polymerase or a derivative or homologue of that enzyme, the production of a recombinant form of the polymerase typically involves the construction of an expression vector, the transformation of a host cell with the vector, and culture of the transformed host cell under conditions such that expression will occur. To construct the expression vector, a DNA is obtained that encodes the mature (used here to include all muteins) enzyme or a fusion of the polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of recombinant polymerase. The recombinant polymerase is isolated from the medium or from the cells; recovery and purification of the protein may not be necessary in some instances, where some impurities may be tolerated.

DEFINITIONS

As used herein, the term "DNA polymerase" encompasses enzymes having hydrolase activity, for example, enzymes capable of use to amplify a template sequence during PCR amplification procedures.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin.

A "coding sequence" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties $2^{nd}$ Ed., T. E. Creighton, W.H. Freeman and Company, New York (1993); Posttranslational Covalent Modification of Proteins, B. C. Johnson, Ed., Academic Press, New York, pp. 1–12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$–$10^6$ fold. However, the term "purified" also includes nucleic acids which have been purified from the remainder of the genomic DNA or from other sequences in a library or other environment by at least one order of magnitude, typically two or three orders, and more typically four or five orders of magnitude.

The term "primer" as used herein refers to an oligonucleotide, whether natural or synthetic, which is capable of acting as a point of initiation of synthesis when placed under conditions in which primer extension is initiated. Synthesis of a primer extension product which is complementary to a nucleic acid strand is initiated in the presence of nucleoside triphosphates and a DNA polymerase or reverse transcriptase enzyme in an appropriate buffer at a suitable temperature. A "buffer" includes cofactors (such as divalent metal ions) and salt (to provide the appropriate ionic strength), adjusted to the desired pH. For invention polymerases, the buffer preferably contains about 60 mM Tris-HCl, pH 10.0, 25 mM NaOAc, 2 mM Mg(OAc)$_2$ to provide divalent magnesium ions, and 0.002% NP-40/Tween-20.

A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template.

The term "primer" may refer to more than one primer, particularly in the case where there is some ambiguity in the information regarding one or both ends of the target region to be amplified. For instance, if a nucleic acid sequence is inferred from a protein sequence, a "primer" is actually a collection of primer oligonucleotides containing sequences representing all possible codon variations based on the degeneracy of the genetic code. One of the primers in this collection will be homologous with the end of the target sequence. Likewise, if a "conserved" region shows significant levels of polymorphism in a population, mixtures of primers can be prepared that will amplify adjacent sequences.

A primer may be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

A primer can be labeled, if desired, by incorporating a label detectable by spectroscopic, photochemical, biochemical, immunochemical, or chemical means. For example, useful labels include 32 p, fluorescent dyes, electron-dense reagents, enzymes (as commonly used in ELISAS), biotin, or haptens and proteins for which antisera or monoclonal antibodies are available. A label can also be used to "capture" the primer, so as to facilitate the immobilization of either the primer or a primer extension product, such as amplified DNA, on a solid support.

The terms "thermostable polymerase" and "thermostable enzyme" as used herein refer to an enzyme which is stable to heat and is heat resistant at extreme high temperatures for four or more hours and which catalyzes combination of the nucleotides in the proper manner to form primer extension products that are complementary to a template nucleic acid strand. Generally, synthesis of a primer extension product begins at the 3' end of the primer and proceeds in the 5' direction along the template strand, until synthesis terminates.

The thermostable enzymes of the present invention satisfy the requirements for effective use in the amplification reaction known as the polymerase chain reaction or PCR as described in U.S. Pat. No. 4,965,188 (incorporated herein by reference). The invention enzymes do not become irreversibly denatured (inactivated) when subjected to the elevated temperatures for the time necessary to effect denaturation of double-stranded nucleic acids, a key step in the PCR process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically range from about 90° C. to about 105° C. for a time depending mainly on the temperature and the nucleic acid length, typically from a few seconds up to four minutes.

Higher temperatures may be required as the buffer salt concentration and/or GC composition of the nucleic acid is increased. The invention enzymes do not become irreversibly denatured from exposures to temperatures of about 95° C. to 113° C. for four hours or more. The extreme thermostability of the invention DNA polymerase enzymes provides additional advantages over previously characterized thermostable enzymes. Prior to the present invention, efficient PCR at denaturation temperatures as high as 113° C. had not been demonstrated. No thermostable DNA polymerases have been described for this purpose. However, as the G/C content of a target nucleic acid increases, the temperature necessary to denature the duplex also increases. For target sequences that require a denaturization step of over 95° C., previous protocols require that solvents are included in the PCR for partially destabilizing the duplex, thus, lowering the effective denaturization temperature.

Agents such as glycerol, DMSO, or formamide have been used in this manner in PCR (Korge et al., 1992, Proc. Natl. Acad. Sci. U.S.A. 89:910-914, and Wong et al., 1991, Nuc. Acids Res. 19:225 1–2259, incorporated herein by reference). However, these agents, in addition to destabilizing duplex DNA, will affect primer stability, can inhibit enzyme activity, and varying concentrations of DMSO or formamide decrease the thermoresistance (i.e., half-life) of thermophilic DNA polymerases. Accordingly, a significant number of optimization experiments and reaction conditions need to be evaluated when utilizing these cosolvents. In contrast, simply raising the denaturization temperature to 100° to 113° C. with the invention DNA polymerases in an otherwise standard PCR can facilitate complete strand separation of PCR product, eliminating the need for DNA helix destabilizing agents.

The extreme hyperthermophilic polymerases disclosed herein are stable at temperatures exceeding 100° C., and even as high as 113° C. without sacrificing the integrity of the target DNA, as is expected with other known polymerases (Ekert and Kunkel, 1992, In PCR: A Practical Approach, eds. McPherson, Quirke and Taylor, Oxford University Press, pages 225-244, incorporated herein by reference).

As used herein, the term "recombinant" means that the nucleic acid is adjacent to "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules. "Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA. "Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan. "Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the gel electrophoresis may be performed to isolate the desired fragment. "Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 60%, 70%, 80%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucin, valine, leucine, or methionine, for another, or substitution of one polar amino acid for another, such as substitution of arginine for lysine, glutamic acid for aspartic acid or glutamine for asparagine). One or more amino acids can be deleted, for example, from a polymerase polypeptide, resulting in modification of the structure of the polypeptide, without significantly altering its biological activity. For example, amino- or carboxyl-terminal amino acids that are not required for polymerase biological activity can be removed.

Polymerase polypeptide sequences of the invention, including those modified as above described, can be assayed for polymerase biological activity by any number of methods, including polymerizing DNA (e.g., the speed and proofreading accuracy of polymerization). For example an assay for the proofreading accuracy of the invention polymerase can include a comparison of the sequence of a DNA polymerized by the invention polymerase with a known sequence for accuracy, and the like.

Polymerase polypeptides included in the invention can have the amino acid sequence of the of polymerase shown in FIG. 1B (SEQ ID NO:2) or 70% homology with SEQ ID NO: 2 wherein the polymerase retains polymerase activity at extreme high temperature, such as temperatures of about 90° C. to 113° C., from about 95° C. to 113° C., from about 100° C. to 107° C., or from about 100° C. to 105° C. Preferably, the polymerase is active at such temperatures for one or more hours, for two or more hours and preferably for four or more hours. "Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "pro-form" molecule, such as a low activity proprotein that can be modified by cleavage to produce a mature polymerase with significantly higher activity. "Hybridization"

refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 ng/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of a polymerase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, ligation reassembly, GSSM and any combination thereof.

In one aspect, the present invention provides a non-stochastic method termed synthetic ligation reassembly (SLR), that is somewhat related to stochastic shuffling, save that the nucleic acid building blocks are not shuffled or concatenated or chimerized randomly, but rather are assembled non-stochastically.

The SLR method does not depend on the presence of a high level of homology between polynucleotides to be shuffled. The invention can be used to non-stochastically generate libraries (or sets) of progeny molecules comprised of over 10100 different chimeras. Conceivably, SLR can even be used to generate libraries comprised of over 101000 different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related polymerases. The polymerases of the present invention can be mutagenized in accordance with the methods described herein.

Thus according to one aspect of the invention, the sequences of a plurality of progenitor nucleic acid templates (e.g., polynucleotides of SEQ ID NO: 1) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In one embodiment, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3' sequence of each finalized chimeric nucleic acid) in each combination is by design (or non-stochastic). Because of the non-stochastic nature of the method, the possibility of unwanted side products is greatly reduced.

In another embodiment, the method provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made genes produced using the invention can also serve as a substrate for recombination with another nucleic acid. Likewise, a man-made gene pathway produced using the invention can also serve as a substrate for recombination with another nucleic acid.

In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A serviceable overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T or N,N,C/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., hybrid polymerases). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular polymerase from different microorganisms. A polymerase encoded by a first polynucleotide from one organism or variant may, for example, function effectively under a particular environmental condition, e.g. high salinity. A polymerase encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures, especially polymerase activity at extreme high temperature, such as a temperature from about 95° C. to 113° C. Some modified polynucleotides may achieve polymerase activity at temperatures up to 150° C., which is presently considered to be the theoretical limit at which life forms could prevent dissolution of the chemical bonds that maintain the integrity of DNA and other essential molecules.

Enzymes encoded by the polynucleotides of the invention include, but are not limited to, hydrolases, such as polymerases. A hybrid polypeptide resulting from the method of the invention may exhibit specialized enzyme activity not displayed in the original enzymes. For example, following recombination and/or reductive reassortment of polynucleotides encoding polymerase activities, the resulting hybrid polypeptide encoded by a hybrid polynucleotide can be screened for specialized polymerase activities obtained from each of the original enzymes, i.e. whether the polymerase has or is free of a 3'–5' exonuclease activity, the DNA extension rate of the polymerase, the % residual activity at altered pH as compared to the wild-type polymerase, and the optimum temperature and upper temperature limit of polymerase activity. Thus, for example, the polymerase may be screened to ascertain those chemical functionalities which distinguish the hybrid polymerase from the original polymerase, for example, the upper limit of thermal stability, the duration of thermal stability at the upper temperature limit, or the pH or salt concentration at which the hybrid polypeptide functions. Additional desirable polymerase characteristics that may be screened for include utility of the hybrid polymerase for PCR of template molecules greater than 20 kb in length or containing greater than 90% guanidine-cytosine (GC) content.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, polymerases that can be produced in a prokaryotic host can be readily scaled up for commercial production. A normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganism from which the invention polynucleotide having SEQ ID NO: 1 is derived is *Pyrolobus fumaria*.

Additional polynucleotides may be prepared from prokaryotic microorganisms, such as *Eubacteria* and *Archaebacteria*, and lower eukaryotic microorganisms such as fungi, some algae and protozoa. Polynucleotides may be isolated from environmental samples, in which case the nucleic acid may be recovered without culturing of an organism or recovered from one or more cultured organisms. In order to have polymerase activity in the range above 90° C. up to 150° C. (e.g., up to 113° C.), such microorganisms are preferably hyperthermophiles that function at temperatures above 100° C. in terrestrial hot springs and deep sea thermal vents. The polymerases produced by hyperthermophiles may have a lower temperature at which enzymatic activity fails. For example, *Pyrolobus fumaria* ceases to grow at a temperature below 90° C.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified polymerase activity at temperatures in the range from 70° C. up to about 113° C. may then be sequenced to identify the polynucleotide sequence encoding the polymerase.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al., 1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for polymerase activities not found in the original gene clusters, or altered from that found in the original gene clusters.

Therefore, in one embodiment, the invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the polynucleotide encoding the hybrid polypeptide.

Methods for screening for polymerase activities are known to those of skill in the art and are discussed throughout the present specification. Such methods may be employed when isolating the polypeptides and polynucleotides of the invention.

As representative examples of expression vectors which may be used there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
a) Primers that include a poly-A head and poly-T tail which when made single-stranded would provide orientation can be utilized. This is accomplished by having the first few bases of the primers made from RNA and hence easily removed RNAseH.
b) Primers that include unique restriction cleavage sites can be utilized. Multiple sites, a battery of unique sequences, and repeated synthesis and ligation steps would be required.
c) The inner few bases of the primer could be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:
1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular amplification reaction (e.g., such as catalytic domain of a DNA polymerase) with a predetermined macromolecule, such as for example a proteinaceous receptor, an oligosaccharide, viron, or other predetermined compound or structure.

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N-3-Adenine, see Sun and Hurley, 1992); an N-acelylated or deacetylated 4'-fluro-4-aminobiphenyl adduct capable of inhibiting DNA synthesis (see, for example, van de Poll et al., 1992); or a N-acetylated or deacetylated 4-aminobiphenyl adduct capable of inhibiting DNA synthesis (see also, van de Poll et al., 1992, pp. 751–758); trivalent chromium, a trivalent chromium salt, a polycyclic aromatic hydrocarbon ("PAH") DNA adduct capable of inhibiting DNA replication, such as 7-bromomethyl-benz[α]anthracene ("BMA"), tris(2,3-dibromopropyl) phosphate ("Tris-BP"), 1,2-dibromo-3-chloropropane ("DBCP"), 2-bromoacrolein (2BA), benzo[α]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N-3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (Gene Site Saturation Mutagenesis™ (GSSM)). The oligos used are comprised contiguously of a first homologous sequence, a degenerate N,N,N sequence, and preferably but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions, and/or substitutions.

In a particular exemplification, it is possible to simultaneously mutagenize two or more contiguous amino acid positions using an oligo that contains contiguous N,N,N triplets, i.e. a degenerate $(N,N,N)_n$ sequence.

In another aspect, the present invention provides for the use of degenerate cassettes having less degeneracy than the N,N,N sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable $E.\ coli$ host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1–500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

One aspect of the invention is an isolated nucleic acid comprising one of the sequences of SEQ ID NO: 1, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of a Group A nucleic acid sequence (or the sequences complementary thereto). The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acids of one of the SEQ ID NO: 1, and sequences substantially identical thereto, may be used to prepare one of the polypeptides of a Group B amino acid sequence, and sequences substantially identical thereto, or fragments comprising at least 5, 10, 15, 20, 25, 30, 35, 40, 50, 75, 100, or 150 consecutive amino acids of one of the polypeptides of SEQ ID NO: 2, and sequences substantially identical thereto.

Accordingly, another aspect of the invention is an isolated nucleic acid which encodes one of the polypeptides of SEQ ID NO: 2, and sequences substantially identical thereto, or fragments comprising at least 5, 10, 15, 20, 25, 30, 35, 40, 50, 75, 100, or 150 consecutive amino acids of one of the polypeptides of the SEQ ID NO: 2. The coding sequences of these nucleic acids may be identical to one of the coding sequences of one of the nucleic acids of SEQ ID NO: 1, or a fragment thereof or may be different coding sequences which encode one of the polypeptides of SEQ ID NO: 2, sequences substantially identical thereto, and fragments having at least 5, 10, 15, 20, 25, 30, 35, 40, 50, 75, 100, or 150 consecutive amino acids of one of the polypeptides of SEQ ID NO: 2, as a result of the redundancy or degeneracy of the genetic code. The genetic code is well known to those of skill in the art and can be obtained, for example, on page 214 of B. Lewin, Genes VI, Oxford University Press, 1997, the disclosure of which is incorporated herein by reference.

The isolated nucleic acid which encodes one of the polypeptides of SEQ ID NO: 2, and sequences substantially identical thereto, may include, but is not limited to: only the coding sequence of one of SEQ ID NO: 1, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only coding sequence for the polypeptide as well as a polynucleotide which includes additional coding and/or non-coding sequence.

Alternatively, the nucleic acid sequences of SEQ ID NO: 1, and sequences substantially identical thereto, may be mutagenized using conventional techniques, such as site directed mutagenesis, or other techniques familiar to those skilled in the art, to introduce silent changes into the polynucleotides of SEQ ID NO: 1, and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of SEQ ID NO: 2, and sequences substantially identical thereto. Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of SEQ ID NO: 1, and sequences substantially identical thereto (or the sequences complementary thereto) under conditions of high, moderate, or low stringency as provided herein.

The isolated nucleic acids of SEQ ID NO: 1, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of SEQ ID NO: 1, and sequences substantially identical thereto, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. Current Protocols in Molecular Biology, John Wiley 503 Sons, Inc. 1997 and Sambrook et al., Molecular Cloning: A Laboratory Manual 2d Ed., Cold Spring Harbor Laboratory Press, 1989, the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", *PCR Methods and Applications* 1:5–16,1991; E. Fahy et al., "Self-sustained Sequence Replication (3SR): An Isothermal Transcription-based Amplification System Alternative to PCR", *PCR Methods and Applications* 1:25–33, 1991; and Walker G. T. et al., "Strand Displacement Amplification-an Isothermal in vitro DNA Amplification Technique", *Nucleic Acid Research* 20:1691–1696, 1992, the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an interculator such as ethidium bromide. Alternatively, one or more of the probes may be labeled with a radioactive isotope and the presence of a radioactive amplification product may be detected by auto-radiography after gel electrophoresis.

Probes derived from sequences near the ends of the sequences of SEQ ID NO: 1, and sequences substantially identical thereto, may also be used in chromosome walking procedures to identify clones containing genomic sequences located adjacent to the sequences of SEQ ID NO: 1, and sequences substantially identical thereto. Such methods allow the isolation of genes which encode additional proteins from the host organism.

The isolated nucleic acids of SEQ ID NO: 1, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of SEQ ID NO: 1, and sequences substantially identical thereto, or the sequences complementary thereto may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2×10^7$ cpm (specific activity $4–9×10^8$ cpm/ug) of $^{32}P$ end-labeled oligonucleotide probe are then added to the solution. After 12–16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m=81.5+16.6(\log [Na+])+0.41(\text{fraction G+C})-(600/N)$ where N is the length of the probe.

If the hybridization is carried out in a solution containing formamide, the melting temperature may be calculated using the equation: $T_m=81.5+16.6(\log [Na+])+0.41(\text{fraction G+C})-(0.63\% \text{ formamide})-(600/N)$ where N is the length of the probe.

Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the $T_m$. Typically, for hybridizations in 6× SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, or at least 70% homology to a nucleic acid sequence selected from the group consisting of one of the sequences of SEQ ID NO: 1, and sequences substantially identical thereto, or fragments comprising at least about 10, 15, 20, 25, 30, 35, 40, 50, 75, 100, 150, 200, 300, 400, or 500 consecutive bases thereof, and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of SEQ ID NO: 1 or the sequences complementary thereto.

Additionally, the above procedures may be used to isolate nucleic acids which encode polypeptides having at least about 99%, 95%, at least 90%, at least 85%, at least 80%, or at least 70% homology to a polypeptide having the sequence of one of SEQ ID NO: 2, and sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising the sequence of one of SEQ ID NO: 1, and sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the E. coli lac or trp promoters, the lad promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the α factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene.

In some embodiments, the nucleic acid encoding one of the polypeptides of SEQ ID NO: 2, and sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of SEQ ID NO: 2, and sequences substantially identical thereto, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2d Ed., Cold Spring Harbor Laboratory Press, 1989, the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the genera *Pseudomonas, Streptomyces*, and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981), and other cell lines capable of expressing proteins from a compatible vector, such as the C 127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of SEQ ID NO: 2, and sequences substantially identical thereto, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID NO: 2, and sequences substantially identical thereto, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of SEQ ID NO: 2, and sequences substantially identical thereto, or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of SEQ ID NO: 2, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., Technique, 1:11–15, 1989) and Caldwell, R. C. & Joyce G. F., PCR Methods Applic., 2:28–33, 1992, the disclosure of which is incorporated herein by reference in its entirety. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. & Sauer, R. T., et al., Science, 241:53–57, 1988, the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in U.S. Pat. No. 5,965,408, filed Jul. 9, 1996, entitled, "Method of DNA Reassembly by Interrupting Synthesis", the disclosure of which is incorporated herein by reference in its entirety.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., PNAS, USA, 91:10747–10751, 1994, the disclosure of which is incorporated herein by reference. Briefly, in such procedures a plurality of nucleic acids to be recombined are digested with DNAse to generate fragments having an average size of 50–200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10–30 ng/µl in a solution of 0.2 mM of each dNTP, 2.2 mM $MgCl2$, 50 mM KCL, 10 mM Tris HCl, pH 9.0, and 0.1% Triton X-100. 2.5 units of Taq polymerase per 100 µl of reaction mixture is added and PCR is performed using the following regime: 94° C. for 60 seconds, 94° C. for 30 seconds, 50–55° C. for 30 seconds, 72° C. for 30 seconds (30–45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations" the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811–7815, 1992, the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., Biotechnology Research, 11: 1548–1552, 1993, the disclosure of which incorporated herein by reference in its entirety. Random and site-directed mutagenesis are described in Arnold, F. H., Current Opinion in Biotechnology, 4:450–455, 1993, the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis", and U.S. Pat. No. 5,939,250, filed May 22, 1996, entitled, "Production of Enzymes Having Desired Activities by Mutagenesis", both of which are incorporated herein by reference.

The variants of the polypeptides of SEQ ID NO: 2 may be variants in which one or more of the amino acid residues of the polypeptides of the SEQ ID NO: 2 are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp and Glu with another acidic residue; replacement of a residue bearing an amide group, such as Asn and Gln, with another residue bearing an amide group; exchange of a basic residue such as Lys and Arg with another basic residue; and replacement of an aromatic residue such as Phe, Tyr with another aromatic residue.

Other variants are those in which one or more of the amino acid residues of the polypeptides of the SEQ ID NO: 2 includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of SEQ ID NO: 2, and sequences substantially identical thereto. In other embodiments, the fragment, derivative, or analog includes a proprotein, such that the fragment, derivative, or analog can be activated by cleavage of the proprotein portion to produce an active polypeptide.

Another aspect of the invention is polypeptides or fragments thereof which have at least about 70%, at least about 80%, at least about 85%, at least about 90%, at least about 95%, or more than about 95% homology to one of the polypeptides of SEQ ID NO: 2, and sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID NO: 2, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NO: 2, and sequences substantially identical thereto, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of SEQ ID NO: 2, and sequences substantially identical thereto, which retain the enzymatic function of the polypeptides of SEQ ID NO: 2, and sequences substantially identical thereto. For example the fragments or variants of said polypeptides, may be used to catalyze biochemical reactions, which indicate that the fragment or variant retains the enzymatic activity of the polypeptides in the SEQ ID NO: 2.

The assay for determining if fragments of variants retain the enzymatic activity of the polypeptides of SEQ ID NO: 2, and sequences substantially identical thereto includes the steps of, contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of SEQ ID NO: 2, and sequences substantially identical thereto or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of SEQ ID NO: 2, and sequences substantially identical thereto or polynucleotides encoding such polypeptides for hydrolyzing glycosidic linkages. In such procedures, a substance containing a glycosidic linkage (e.g., a starch) is contacted with one of the polypeptides of SEQ ID NO: 2, or sequences substantially identical thereto under conditions which facilitate the hydrolysis of the glycosidic linkage.

The polypeptides of SEQ ID NO: 2, and sequences substantially identical thereto or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of SEQ ID NO: 2, and sequences substantially identical thereto, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of SEQ ID NO: 2, and sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of SEQ ID NO: 2, and sequences substantially identical thereto, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 2:495–497, 1975, the disclosure of which is incorporated herein by reference), the trioma technique, the human B-cell hybridoma technique (Kozbor et al., Immunology Today 4:72, 1983, the disclosure of which is incorporated herein by reference), and the EBV-hybridoma technique (Cole, et al., 1985, in Monoclonal Antibodies and Cancer Therapy, Alan R. Liss, Inc., pp. 77–96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of SEQ ID NO: 2, and sequences substantially identical thereto, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of SEQ ID NO: 2, and sequences substantially identical thereto, or fragments comprising at least 5, 10, 15, 20, 25, 30, 35, 40, 50, 75, 100, or 1.50 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology*, Vol 160, pp. 87–116, which is hereby incorporated by reference in its entirety.

As used herein the term "nucleic acid sequence as set forth in SEQ ID NO: 1" encompasses the nucleotide sequences of SEQ ID NO: 1, and sequences substantially identical thereto, as well as sequences homologous to SEQ ID NO: 1, and fragments thereof and sequences complementary to all of the preceding sequences. The fragments include portions of SEQ ID NO: 1, comprising at least 10, 15, 20, 25, 30, 35, 40, 50, 75, 100, 150, 200, 300, 400, or 500 consecutive nucleotides of SEQ ID NO: 1, and sequences substantially identical thereto. Homologous sequences and fragments of SEQ ID NO: 1, and sequences substantially identical thereto, refer to a sequence having at least 99%, 98%, 97%, 96%, 95%, 90%, 85%, 80%, 75% or 70% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in the SEQ ID NO: 1. The homologous sequences may be obtained using any of the procedures described herein or may result from the correction of a sequencing error. It will be appreciated that the nucleic acid sequences as set forth in SEQ ID NO: 1, and sequences substantially identical thereto, can be represented in the traditional single character format (See the inside back cover of Stryer, Lubert. *Biochemistry*, $3^{rd}$ edition. W. H Freeman & Co., New York.) or in any other format which records the identity of the nucleotides in a sequence.

As used herein the term "a polypeptide sequence as set forth in SEQ ID NO: 2" encompasses the polypeptide sequence of SEQ ID NO: 2, and sequences substantially identical thereto, which are encoded by a sequence as set forth in SEQ ID NO: 1, polypeptide sequences homologous to the polypeptides of SEQ ID NO: 2, and sequences substantially identical thereto, or fragments of any of the preceding sequences. Homologous polypeptide sequences refer to a polypeptide sequence having at least 99%, 98%, 97%, 96%, 95%, 90%, 85%, 80%, 75% or 70% homology to one of the polypeptide sequences of the SEQ ID NO: 2. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of SEQ ID NO: 2, and sequences substantially identical thereto. It will be appreciated that the polypeptide codes as set forth in SEQ ID NO: 2, and sequences substantially identical thereto, can be represented in the traditional single character format or three letter format (See the inside back cover of Starrier, Lubert. *Biochemistry*, $3^{rd}$ edition. W. H Freeman & Co., New York.) or in any other format which relates the identity of the polypeptides in a sequence.

It will be appreciated by those skilled in the art that a nucleic acid sequence as set forth SEQ ID NO: 1 and a polypeptide sequence as set forth in SEQ ID NO: 2 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences as set forth in SEQ ID NO: 1, and sequences substantially identical thereto, one or more of the polypeptide sequences as set forth in SEQ ID NO: 2, and sequences substantially identical thereto. Another aspect of the invention is a computer readable medium having recorded thereon at least 2, 5, 10, 15, or 20 nucleic acid sequences as set forth in SEQ ID NO: 1, and sequences substantially identical thereto.

Another aspect of the invention is a computer readable medium having recorded thereon one or more of the nucleic acid sequences as set forth in SEQ ID NO: 1, and sequences substantially identical thereto. Another aspect of the invention is a computer readable medium having recorded thereon one or more of the polypeptide sequences as set forth in SEQ ID NO: 2, and sequences substantially identical thereto. Another aspect of the invention is a computer readable medium having recorded thereon at least 2, 5, 10, 15, or 20 of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the invention include systems (e.g., internet based systems), particularly computer systems which store and manipulate the sequence information described herein. One example of a computer system 100 is illustrated in block diagram form in FIG. 2. As used herein, "a computer system" refers to the hardware components, software components, and data storage components used to analyze a nucleotide sequence of a nucleic acid sequence as set forth in SEQ ID NO: 1, and sequences substantially identical thereto, or a polypeptide sequence as set forth in the SEQ ID NO: 2. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a–c in a network or wide area network to provide centralized access to the computer system 100.

Software for accessing and processing the nucleotide sequences of a nucleic acid sequence as set forth in SEQ ID NO: 1, and sequences substantially identical thereto, or a polypeptide sequence as set forth in SEQ ID NO: 2, and sequences substantially identical thereto, (such as search tools, compare tools, and modeling tools etc.) may reside in main memory 115 during execution.

In some embodiments, the computer system 100 may further comprise a sequence comparison algorithm for comparing a nucleic acid sequence as set forth in SEQ ID NO: 1, and sequences substantially identical thereto, or a polypeptide sequence as set forth in SEQ ID NO: 2, and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence as set forth in SEQ ID NO: 1, and sequences substantially identical thereto, or a polypeptide sequence as set forth in SEQ ID NO: 2, and sequences substantially identical thereto, stored on a computer readable medium to reference sequences stored on a computer readable medium to identify homologies or structural motifs. Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, Proc. Natl. Acad. Sci. USA 85(8):2444–2448, 1988; Altschul et al., J. Mol. Biol. 215(3):403–410, 1990; Thompson et al., Nucleic Acids Res. 22(2):4673–4680, 1994; Higgins et al., Methods Enzymol. 266:383–402, 1996; Altschul et al., J. Mol. Biol. 215(3):403–410, 1990; Altschul et al., Nature Genetics 3:266–272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence maybe compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for similarity method of person & Lipman, Proc. Natl. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLXN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet.

One example of a useful algorithm is BLAST and BLAST 2.0 algorithms, which are described in Altschul et al., Nuc. Acids Rest 25:3389–3402, 1977, and Altschul et al., J. Mol. Biol. 215:403–410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased cumulative scores are calculated using, for nucleotide sequences, the parameters M (reward score for a pair of matching residues; always>0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative scoring residue alignments; or the end of either sequence is reached. The BLAST algorithm parameters W, T, and X determine the sensitivity and speed of the alignment. The BLASTN program (for nucleotide sequences) use as defaults a wordlength (W) of 11, an expectation (E) of 10, M=5, N=4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:
  (1) BLASTP and BLAST3 compare an amino acid query sequence against a protein sequence database;
  (2) BLASTN compares a nucleotide query sequence against a nucleotide sequence database;
  (3) BLASTX compares the six-frame conceptual translation products of a query nucleotide sequence (both strands) against a protein sequence database;
  (4) TBLASTN compares a query protein sequence against a nucleotide sequence database translated in all six reading frames (both strands); and
  (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443–1445, 1992; Henikoff and Henikoff, Proteins 17:49–61, 1993). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine, e.g., at [[www.ncbi.nlm.nih.gov]].

The parameters used with the above algorithms may be adapted depending on the sequence length and degree of homology studied. In some embodiments, the parameters may be the default parameters used by the algorithms in the absence of instructions from the user.

Figure 3:
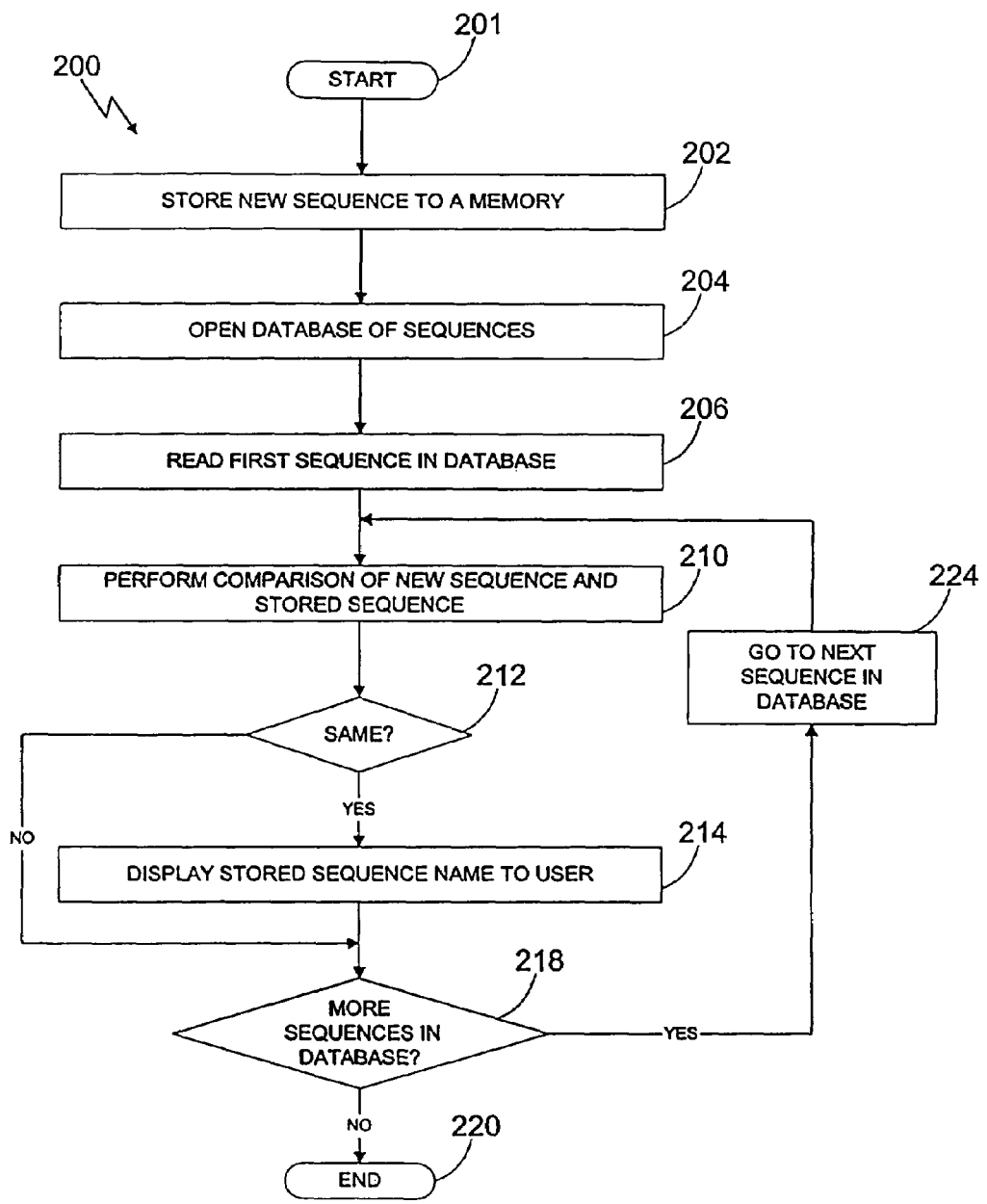
FIG. 3 is a flow diagram illustrating one embodiment of a process for comparing a new nucleotide or protein sequence with a database of sequences in order to determine the homology levels between the new sequence and the sequences in the database.

FIG. 3 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence as set forth in SEQ ID NO: 1, and sequences substantially identical thereto, or a polypeptide sequence as set forth in SEQ ID NO: 2, and sequences substantially identical thereto, a data storage device having retrievably stored thereon reference nucleotide sequences or polypeptide sequences to be compared to a nucleic acid sequence as set forth in SEQ ID NO: 1, and sequences substantially identical thereto, or a polypeptide sequence as set forth in SEQ ID NO: 1, and sequences substantially identical thereto, and a sequence comparer for conducting the comparison. The sequence comparer may indicate a homology level between the sequences compared or identify structural motifs in the above described nucleic acid code of SEQ ID NO: 1, and sequences substantially identical thereto, or a polypeptide sequence as set forth in SEQ ID NO: 2, and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences as set forth in SEQ ID NO: 1, and sequences substantially identical thereto, or the polypeptide sequences as set forth in SEQ ID NO: 2, and sequences substantially identical thereto.

Another aspect of the invention is a method for determining the level of homology between a nucleic acid sequence as set forth in SEQ ID NO: 1, and sequences substantially identical thereto, or a polypeptide sequence as set forth in SEQ ID NO: 2, and sequences substantially identical thereto, and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences as set forth in the SEQ ID NO: 1, or the polypeptide sequences as set forth in the Group B nucleic acid sequences through use of the computer program and determining homology between the nucleic acid codes or polypeptide codes and reference nucleotide sequences or polypeptide sequences.

Figure 4:
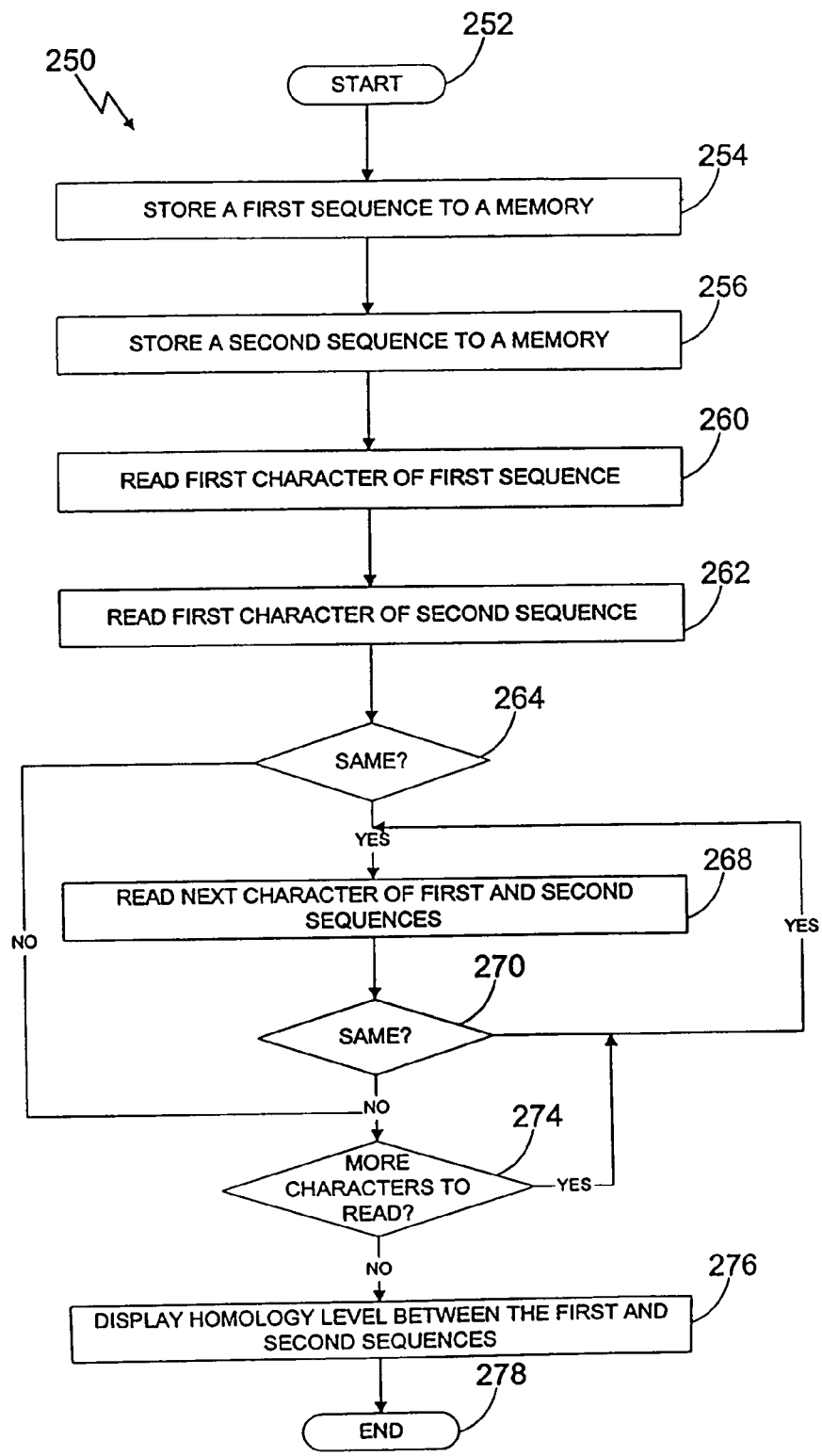
FIG. 4 is a flow diagram illustrating one embodiment of a process in a computer for determining whether two sequences are homologous.

FIG. 4 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of SEQ ID NO: 1, and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence as set forth in SEQ ID NO: 1, and sequences substantially identical thereto. In one embodiment, the computer program may be a program which determines whether a nucleic acid sequence as set forth in SEQ ID NO: 1, and sequences substantially identical thereto, contains a single nucleotide polymorphism (SNP) with respect to a reference nucleotide sequence.

Accordingly, another aspect of the invention is a method for determining whether a nucleic acid sequence as set forth in SEQ ID NO: 1, and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 4. The method may also be performed by reading at least 2, 5, 10, 15, 20, 25, 30, or 40 or more of the nucleic acid sequences as set forth in SEQ ID NO: 1, and sequences substantially identical thereto, and the reference nucleotide sequences through the use of the computer program and identifying differences between the nucleic acid codes and the reference nucleotide sequences with the computer program.

In other embodiments the computer based system may further comprise an identifier for identifying features within a nucleic acid sequence as set forth in the SEQ ID NO: 1 or a polypeptide sequence as set forth in SEQ ID NO: 2, and sequences substantially identical thereto.

An "identifier" refers to one or more programs which identifies certain features within a nucleic acid sequence as set forth in SEQ ID NO: 1, and sequences substantially identical thereto, or a polypeptide sequence as set forth in SEQ ID NO: 2, and sequences substantially identical thereto. In one embodiment, the identifier may comprise a program which identifies an open reading frame in a nucleic acid sequence as set forth in SEQ ID NO: 1, and sequences substantially identical thereto.

Figure 5:
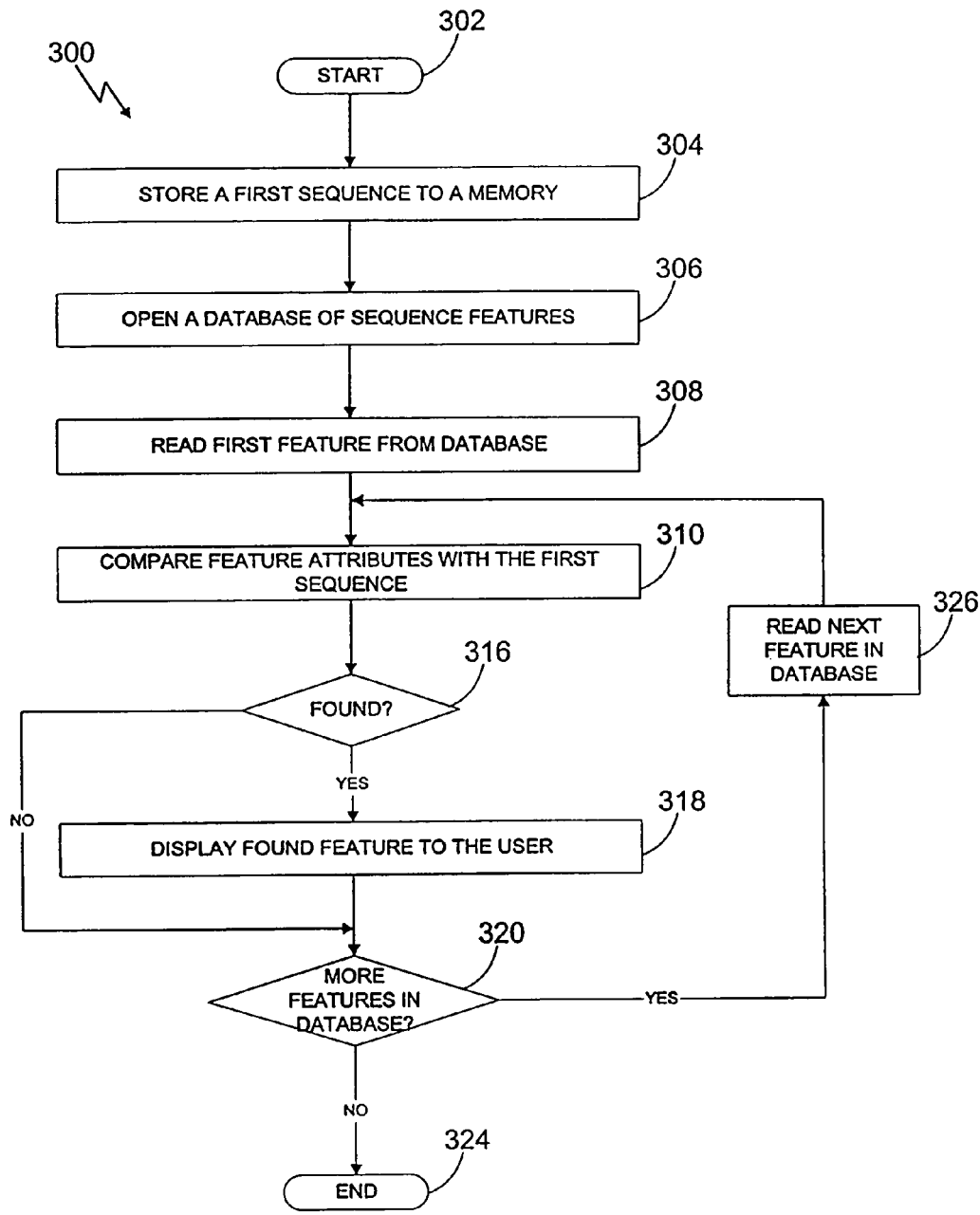
FIG. 5 is a flow diagram illustrating one embodiment of an identifier process 300 for detecting the presence of a feature in a sequence.

FIG. 5 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence as set forth in SEQ ID NO: 1, and sequences substantially identical thereto, or a polypeptide sequence as set forth in SEQ ID NO: 2, and sequences substantially identical thereto, comprising reading the nucleic acid code(s) or polypeptide code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, or 40 of the nucleic acid sequences as set forth in SEQ ID NO: 1, and sequences substantially identical thereto, or the polypeptide sequences as set forth in SEQ ID NO: 2, and sequences substantially identical thereto, through the use of the computer program and identifying features within the nucleic acid codes or polypeptide codes with the computer program.

A nucleic acid sequence as set forth in SEQ ID NO: 1, and sequences substantially identical thereto, or a polypeptide sequence as set forth in SEQ ID NO: 2, and sequences substantially identical thereto, may be stored and manipulated in a variety of data processor programs in a variety of formats. For example, a nucleic acid sequence as set forth in SEQ ID NO: 1, and sequences substantially identical thereto, or a polypeptide sequence as set forth in SEQ ID NO: 2, and sequences substantially identical thereto, may be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence as set forth in SEQ ID NO: 1, and sequences substantially identical thereto, or a polypeptide sequence as set forth in SEQ ID NO: 2, and sequences substantially identical thereto. The following list is intended not to limit the invention but to provide guidance to programs and databases which are useful with the nucleic acid sequences as set forth in SEQ ID NO: 1, and sequences substantially identical thereto, or the polypeptide sequences as set forth in SEQ ID NO: 2, and sequences substantially identical thereto.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237–245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The invention will be further described with reference to the following examples; however, it is to be understood that the invention is not limited to such examples.

EXAMPLE 1

Optimization tests were conducted to determine the most favorable conditions for utilizing the DNA polymerase of SEQ ID NO: 2 for polymerase activity in PCR at temperatures in the range from 85° C. to 95° C. The parameters tested were buffer, pH, salt and salt concentration, Mg ion source, detergent and detergent concentration.

The buffers tested were Tris-HCl, Tris-HOAc, phosphate buffer, Bicine, HEPES, MOPS, and TAPS. The most ideal buffer was Tris HCl.

The pH range tested was from 7.5 to 10.0. The most ideal pH was 10.0.

The salts tested were NaCl, NaOAc, KCl, $(NH_4)_2SO_4$, $NH_4OAc$, and LiCl at concentrations from 5 mM to 200 mM. The most favorable salt was 25 mM NaOAc.

The magnesium ion sources tested were $MgCl_2$, $Mg(OAc)_2$, $MgSO_4$ at concentrations from 0.5 mM to 5 mM. The most favorable of these was 2 to 2.5 mM $Mg(KOAc)_2$.

The detergents tested were NP-40, Tween-20®, and Triton X-100® detergents at concentrations of 0.001T to 0.5% by volume. The best condition was 0.002% concentration of a mixture of NP-40 and Tween-20 detergents.

In view of these results, it was concluded that the most favorable buffer for conducting PCR using the DNA polymerase of SEQ ID NO:2 utilizes 60 mM Tris-HCl, pH 10.0, 25 mM NaOAc, 2 mM Mg(OAc)2, and 0.002% NP-40/Tween-20.

While the invention has been described in detail with reference to certain preferred embodiments thereof, it will be understood that modifications and variations are within the spirit and scope of that which is described and claimed.

What is claimed is:

1. A method of generating a nucleic acid that encodes a polypeptide having a polymerase activity comprising:

obtaining a nucleic acid comprising a sequence as set forth in SEQ ID NO:1, or its complement;

modifying one or more nucleotides in said sequence to another nucleotide, deleting one or more nucleotides in said sequence, or adding one or more nucleotides to said sequence, to generate a variant nucleic acid that encodes a polypeptide having polymerase activity;

expressing the variant nucleic acid to generate a polypeptide; and screening the polypeptide for a polymerase activity, thereby generating a nucleic acid encoding a polypeptide having a polymerase activity.

* * * * *

SEQUENCE LISTING

```
<160> NUMBER OF SEQ ID NOS: 2

<210> SEQ ID NO 1
<211> LENGTH: 2412
<212> TYPE: DNA
<213> ORGANISM: Pyrolobus fumarius
<220> FEATURE:
<221> NAME/KEY: CDS
<222> LOCATION: (1)..(2412)

<400> SEQUENCE: 1 atg act gaa gtt gta ttc acg gtt tta gac tct agc tac gag gtt gtt      48
Met Thr Glu Val Val Phe Thr Val Leu Asp Ser Ser Tyr Glu Val Val
1               5                   10                  15
```

```
ggt aaa gag cct cag gta atc ata tgg ggt att gct gag aac ggc gag      96
Gly Lys Glu Pro Gln Val Ile Ile Trp Gly Ile Ala Glu Asn Gly Glu
         20                  25                  30 agg gta gtc ctc att gac agg tct ttt cgc cca tac ttc tat gcg ctg     144
Arg Val Val Leu Ile Asp Arg Ser Phe Arg Pro Tyr Phe Tyr Ala Leu
     35                  40                  45 ctt gca ccg ggc gcc gat cct aag cag gta gca caa cgt att cgt gca     192
Leu Ala Pro Gly Ala Asp Pro Lys Gln Val Ala Gln Arg Ile Arg Ala
 50                  55                  60 ttg agt agg cca aag agc ccg att ata ggt gta gag gat gac aag agg     240
Leu Ser Arg Pro Lys Ser Pro Ile Ile Gly Val Glu Asp Asp Lys Arg
 65                  70                  75                  80 aag tac ttc ggg agg cct cgt agg gtc tta cgt att cgc acc gtg cta     288
Lys Tyr Phe Gly Arg Pro Arg Arg Val Leu Arg Ile Arg Thr Val Leu
                 85                  90                  95 ccc gag gct gtt agg gag tat cgc gaa ctc gta aag aac gtt gat ggt     336
Pro Glu Ala Val Arg Glu Tyr Arg Glu Leu Val Lys Asn Val Asp Gly
            100                 105                 110 gtt gag gat gtt cta gag gcg gat ata cgc ttc gct atg cgc tat ctc     384
Val Glu Asp Val Leu Glu Ala Asp Ile Arg Phe Ala Met Arg Tyr Leu
        115                 120                 125 ata gat cac gat cta ttt cct ttc acc tgg tac cgt gta gag gct gag     432
Ile Asp His Asp Leu Phe Pro Phe Thr Trp Tyr Arg Val Glu Ala Glu
130                 135                 140 ccc ctc gag aac aag atg ggc ttc cgt gtc gac aag gta tac ctg gtt     480
Pro Leu Glu Asn Lys Met Gly Phe Arg Val Asp Lys Val Tyr Leu Val
145                 150                 155                 160 aag agc agg ccg gag cca ctt tat ggt gag gct ctc gca cca acc aag     528
Lys Ser Arg Pro Glu Pro Leu Tyr Gly Glu Ala Leu Ala Pro Thr Lys
                165                 170                 175 ctt ccc gat ctt agg ata ctc gcg ttc gat att gaa gtt tat agc aag     576
Leu Pro Asp Leu Arg Ile Leu Ala Phe Asp Ile Glu Val Tyr Ser Lys
            180                 185                 190 caa ggg tcg ccg cgt cca gag cgc gat cct gta ata gtg ata gct gtg     624
Gln Gly Ser Pro Arg Pro Glu Arg Asp Pro Val Ile Val Ile Ala Val
        195                 200                 205 aag act gac gat ggc gat gag gtg cta ttc att gca gag ggc aaa gac     672
Lys Thr Asp Asp Gly Asp Glu Val Leu Phe Ile Ala Glu Gly Lys Asp
    210                 215                 220 gat cga aaa ccg ata cgc gag ttt gta gag tac gtg aag agg tat gac     720
Asp Arg Lys Pro Ile Arg Glu Phe Val Glu Tyr Val Lys Arg Tyr Asp
225                 230                 235                 240 ccc gac ata ata gtc ggt tat aac aac aat cat ttc gat tgg cct tat     768
Pro Asp Ile Ile Val Gly Tyr Asn Asn Asn His Phe Asp Trp Pro Tyr
                245                 250                 255 ctt ttg agg cgc gcc cgc atc cta ggc ata aag ctt gat gtg act aga     816
Leu Leu Arg Arg Ala Arg Ile Leu Gly Ile Lys Leu Asp Val Thr Arg
            260                 265                 270 aga gtt ggc gcc gag ccc acc act agc gta cat ggg cac gtc tct gtc     864
Arg Val Gly Ala Glu Pro Thr Thr Ser Val His Gly His Val Ser Val
        275                 280                 285 cct ggc agg ctt aac gta gat ctg tac gac tat gcc gaa gag atg cca     912
Pro Gly Arg Leu Asn Val Asp Leu Tyr Asp Tyr Ala Glu Glu Met Pro
    290                 295                 300 gag atc aag ata aag agt ctc gag gag gtc gca gag tat cta ggc gtg     960
Glu Ile Lys Ile Lys Ser Leu Glu Glu Val Ala Glu Tyr Leu Gly Val
305                 310                 315                 320 atg aag aag agt gaa cgc gtt atc atc aat tgg tgg gag att cca gac    1008
Met Lys Lys Ser Glu Arg Val Ile Ile Asn Trp Trp Glu Ile Pro Asp
                325                 330                 335
```

```
tat tgg gac gac ccg aag aag aga cca cta tta ctg caa tac gcg cgc      1056
Tyr Trp Asp Asp Pro Lys Lys Arg Pro Leu Leu Leu Gln Tyr Ala Arg
            340                 345                 350 gac gat gtc cgc gct act tac ggc tta gcc gag aag ata ttg ccg ttt      1104
Asp Asp Val Arg Ala Thr Tyr Gly Leu Ala Glu Lys Ile Leu Pro Phe
                355                 360                 365 gct atc cag ttg tcg tac gta aca ggt ctc cca cta gac cag gta ggt      1152
Ala Ile Gln Leu Ser Tyr Val Thr Gly Leu Pro Leu Asp Gln Val Gly
        370                 375                 380 gcg atg agt gtt ggc ttt cga ctt gaa tgg tac ctg ata cgc gcg gcg      1200
Ala Met Ser Val Gly Phe Arg Leu Glu Trp Tyr Leu Ile Arg Ala Ala
385                 390                 395                 400 ttt aag atg aaa gag ctt gtg ccg aac cgc gtt gag cgc cca gaa gag      1248
Phe Lys Met Lys Glu Leu Val Pro Asn Arg Val Glu Arg Pro Glu Glu
                    405                 410                 415 act tac cgt ggc gct ata gtt ctt gag ccg ttg aga ggc gtg cac gag      1296
Thr Tyr Arg Gly Ala Ile Val Leu Glu Pro Leu Arg Gly Val His Glu
                420                 425                 430 aat ata gcc gta ctc gac ttt agc tcg atg tac cca aac atc atg ata      1344
Asn Ile Ala Val Leu Asp Phe Ser Ser Met Tyr Pro Asn Ile Met Ile
            435                 440                 445 aag tac aat gtt ggt cct gac acg ctt gtg agg cct ggt gaa aag tgt      1392
Lys Tyr Asn Val Gly Pro Asp Thr Leu Val Arg Pro Gly Glu Lys Cys
        450                 455                 460 ggc gag tgt ggt tgc tgg gag gcc ccg gag gtc aag cac agg ttc cgt      1440
Gly Glu Cys Gly Cys Trp Glu Ala Pro Glu Val Lys His Arg Phe Arg
465                 470                 475                 480 agg tgt ccg ccc ggc ttc ttc aag aca gtt ctt gag agg ctg tta gag      1488
Arg Cys Pro Pro Gly Phe Phe Lys Thr Val Leu Glu Arg Leu Leu Glu
                    485                 490                 495 ctt cgt aag cgt gtg cgt gct gaa atg aag aag tat cct ccg gat agc      1536
Leu Arg Lys Arg Val Arg Ala Glu Met Lys Lys Tyr Pro Pro Asp Ser
                500                 505                 510 cca gaa tat cga ctg ttg gat gaa agg cag aag gcg ttg aag gtt ctt      1584
Pro Glu Tyr Arg Leu Leu Asp Glu Arg Gln Lys Ala Leu Lys Val Leu
            515                 520                 525 gca aac gct agt tac ggc tac atg ggt tgg agc ggc gct agg tgg tat      1632
Ala Asn Ala Ser Tyr Gly Tyr Met Gly Trp Ser Gly Ala Arg Trp Tyr
        530                 535                 540 tgc agg gag tgc gca aag gct gtc acg gct tgg ggt agg cac ctc ata      1680
Cys Arg Glu Cys Ala Lys Ala Val Thr Ala Trp Gly Arg His Leu Ile
545                 550                 555                 560 cgc acc gcc atc aac ata gct cgt aaa cta ggc ctc aag gtg atc tac      1728
Arg Thr Ala Ile Asn Ile Ala Arg Lys Leu Gly Leu Lys Val Ile Tyr
                    565                 570                 575 ggt gac aca gat tcg ctc ttc gtg acc tat gat ccg gag aag gtg gaa      1776
Gly Asp Thr Asp Ser Leu Phe Val Thr Tyr Asp Pro Glu Lys Val Glu
                580                 585                 590 aat ttc atc aaa att ata aag gag gag ctg ggg ttc gaa atc aag cta      1824
Asn Phe Ile Lys Ile Ile Lys Glu Glu Leu Gly Phe Glu Ile Lys Leu
            595                 600                 605 gag aag gtg tac aaa cgc tta ttc ttt aca gag gct aag aag agg tac      1872
Glu Lys Val Tyr Lys Arg Leu Phe Phe Thr Glu Ala Lys Lys Arg Tyr
        610                 615                 620 gct ggc ctt ctc gag gac gga cgt ata gat att gtc ggt ttc gag gct      1920
Ala Gly Leu Leu Glu Asp Gly Arg Ile Asp Ile Val Gly Phe Glu Ala
625                 630                 635                 640 gta cgt ggc gat tgg tgt gaa ctc gcc aag gag gtt cag act aag gtt      1968
Val Arg Gly Asp Trp Cys Glu Leu Ala Lys Glu Val Gln Thr Lys Val
```

-continued

```
                   645                 650                 655
gtc gaa ata gta ttg aag acg agt gag gtg aac aag gct gta gag tac    2016
Val Glu Ile Val Leu Lys Thr Ser Glu Val Asn Lys Ala Val Glu Tyr
                660                 665                 670 gtc agg aag att gtg aaa gag ttg gag gag ggc aag gtt ccc ata gag    2064
Val Arg Lys Ile Val Lys Glu Leu Glu Glu Gly Lys Val Pro Ile Glu
            675                 680                 685 aag ctt gta atc tgg aag acc ctt agt aag cgt ctt gag gag tac aca    2112
Lys Leu Val Ile Trp Lys Thr Leu Ser Lys Arg Leu Glu Glu Tyr Thr
        690                 695                 700 acg gag gca cca cac gtc gtt gca gcg aag agg atg ctg tca gca ggc    2160
Thr Glu Ala Pro His Val Val Ala Ala Lys Arg Met Leu Ser Ala Gly
705                 710                 715                 720 tac cgg gta agc cca ggc gac aag ata ggg tat gta ata gtg aag ggt    2208
Tyr Arg Val Ser Pro Gly Asp Lys Ile Gly Tyr Val Ile Val Lys Gly
                725                 730                 735 ggt ggc cgt atc agt caa aga gca tgg cca tac ttc atg gtc aag gat    2256
Gly Gly Arg Ile Ser Gln Arg Ala Trp Pro Tyr Phe Met Val Lys Asp
            740                 745                 750 cct agc cag ata gac gtg acc tac tat gtt gac cac caa atc atc ccg    2304
Pro Ser Gln Ile Asp Val Thr Tyr Tyr Val Asp His Gln Ile Ile Pro
        755                 760                 765 gct gca ttg aga ata ctg ggc tac ttt ggc atc acc gag aag aag ctg    2352
Ala Ala Leu Arg Ile Leu Gly Tyr Phe Gly Ile Thr Glu Lys Lys Leu
    770                 775                 780 aaa gca agt gca act ggg cag aag act ctc ttc gac ttt cta gcc aag    2400
Lys Ala Ser Ala Thr Gly Gln Lys Thr Leu Phe Asp Phe Leu Ala Lys
785                 790                 795                 800 aag agc aag taa                                                    2412
Lys Ser Lys
```

<210> SEQ ID NO 2
<211> LENGTH: 803
<212> TYPE: PRT
<213> ORGANISM: Pyrolobus fumarius

<400> SEQUENCE: 2

```
Met Thr Glu Val Val Phe Thr Val Leu Asp Ser Ser Tyr Glu Val Val
1               5                   10                  15

Gly Lys Glu Pro Gln Val Ile Ile Trp Gly Ile Ala Glu Asn Gly Glu
            20                  25                  30

Arg Val Val Leu Ile Asp Arg Ser Phe Arg Pro Tyr Phe Tyr Ala Leu
        35                  40                  45

Leu Ala Pro Gly Ala Asp Pro Lys Gln Val Ala Gln Arg Ile Arg Ala
    50                  55                  60

Leu Ser Arg Pro Lys Ser Pro Ile Ile Gly Val Glu Asp Lys Arg
65                  70                  75                  80

Lys Tyr Phe Gly Arg Pro Arg Val Leu Arg Ile Arg Thr Val Leu
                85                  90                  95

Pro Glu Ala Val Arg Glu Tyr Arg Glu Leu Val Lys Asn Val Asp Gly
            100                 105                 110

Val Glu Asp Val Leu Glu Ala Asp Ile Arg Phe Ala Met Arg Tyr Leu
        115                 120                 125

Ile Asp His Asp Leu Phe Pro Phe Thr Trp Tyr Arg Val Glu Ala Glu
    130                 135                 140

Pro Leu Glu Asn Lys Met Gly Phe Arg Val Asp Lys Val Tyr Leu Val
145                 150                 155                 160
```

```
Lys Ser Arg Pro Glu Pro Leu Tyr Gly Glu Ala Leu Ala Pro Thr Lys
            165                 170                 175
Leu Pro Asp Leu Arg Ile Leu Ala Phe Asp Ile Glu Val Tyr Ser Lys
            180                 185                 190
Gln Gly Ser Pro Arg Pro Glu Arg Asp Pro Val Ile Val Ile Ala Val
            195                 200                 205
Lys Thr Asp Asp Gly Asp Glu Val Leu Phe Ile Ala Glu Gly Lys Asp
210                 215                 220
Asp Arg Lys Pro Ile Arg Glu Phe Val Glu Tyr Val Lys Arg Tyr Asp
225                 230                 235                 240
Pro Asp Ile Ile Val Gly Tyr Asn Asn Asn His Phe Asp Trp Pro Tyr
                245                 250                 255
Leu Leu Arg Arg Ala Arg Ile Leu Gly Ile Lys Leu Asp Val Thr Arg
            260                 265                 270
Arg Val Gly Ala Glu Pro Thr Thr Ser Val His Gly His Val Ser Val
        275                 280                 285
Pro Gly Arg Leu Asn Val Asp Leu Tyr Asp Tyr Ala Glu Glu Met Pro
    290                 295                 300
Glu Ile Lys Ile Lys Ser Leu Glu Glu Val Ala Glu Tyr Leu Gly Val
305                 310                 315                 320
Met Lys Lys Ser Glu Arg Val Ile Ile Asn Trp Trp Glu Ile Pro Asp
                325                 330                 335
Tyr Trp Asp Asp Pro Lys Lys Arg Pro Leu Leu Gln Tyr Ala Arg
            340                 345                 350
Asp Asp Val Arg Ala Thr Tyr Gly Leu Ala Glu Lys Ile Leu Pro Phe
        355                 360                 365
Ala Ile Gln Leu Ser Tyr Val Thr Gly Leu Pro Leu Asp Gln Val Gly
    370                 375                 380
Ala Met Ser Val Gly Phe Arg Leu Glu Trp Tyr Leu Ile Arg Ala Ala
385                 390                 395                 400
Phe Lys Met Lys Glu Leu Val Pro Asn Arg Val Glu Arg Pro Glu Glu
                405                 410                 415
Thr Tyr Arg Gly Ala Ile Val Leu Glu Pro Leu Arg Gly Val His Glu
            420                 425                 430
Asn Ile Ala Val Leu Asp Phe Ser Ser Met Tyr Pro Asn Ile Met Ile
        435                 440                 445
Lys Tyr Asn Val Gly Pro Asp Thr Leu Val Arg Pro Gly Glu Lys Cys
    450                 455                 460
Gly Glu Cys Gly Cys Trp Glu Ala Pro Glu Val Lys His Arg Phe Arg
465                 470                 475                 480
Arg Cys Pro Pro Gly Phe Phe Lys Thr Val Leu Glu Arg Leu Leu Glu
                485                 490                 495
Leu Arg Lys Arg Val Arg Ala Glu Met Lys Lys Tyr Pro Pro Asp Ser
            500                 505                 510
Pro Glu Tyr Arg Leu Leu Asp Glu Arg Gln Lys Ala Leu Lys Val Leu
        515                 520                 525
Ala Asn Ala Ser Tyr Gly Tyr Met Gly Trp Ser Gly Ala Arg Trp Tyr
    530                 535                 540
Cys Arg Glu Cys Ala Lys Ala Val Thr Ala Trp Gly Arg His Leu Ile
545                 550                 555                 560
Arg Thr Ala Ile Asn Ile Ala Arg Lys Leu Gly Leu Lys Val Ile Tyr
                565                 570                 575
Gly Asp Thr Asp Ser Leu Phe Val Thr Tyr Asp Pro Glu Lys Val Glu
```

-continued

```
            580                 585                 590
Asn Phe Ile Lys Ile Ile Lys Glu Glu Leu Gly Phe Glu Ile Lys Leu
            595                 600                 605
Glu Lys Val Tyr Lys Arg Leu Phe Phe Thr Glu Ala Lys Lys Arg Tyr
            610                 615                 620
Ala Gly Leu Leu Glu Asp Gly Arg Ile Asp Ile Val Gly Phe Glu Ala
625                 630                 635                 640
Val Arg Gly Asp Trp Cys Glu Leu Ala Lys Glu Val Gln Thr Lys Val
                    645                 650                 655
Val Glu Ile Val Leu Lys Thr Ser Glu Val Asn Lys Ala Val Glu Tyr
                660                 665                 670
Val Arg Lys Ile Val Lys Glu Leu Glu Glu Gly Lys Val Pro Ile Glu
            675                 680                 685
Lys Leu Val Ile Trp Lys Thr Leu Ser Lys Arg Leu Glu Glu Tyr Thr
        690                 695                 700
Thr Glu Ala Pro His Val Val Ala Ala Lys Arg Met Leu Ser Ala Gly
705                 710                 715                 720
Tyr Arg Val Ser Pro Gly Asp Lys Ile Gly Tyr Val Ile Val Lys Gly
                725                 730                 735
Gly Gly Arg Ile Ser Gln Arg Ala Trp Pro Tyr Phe Met Val Lys Asp
            740                 745                 750
Pro Ser Gln Ile Asp Val Thr Tyr Tyr Val Asp His Gln Ile Ile Pro
        755                 760                 765
Ala Ala Leu Arg Ile Leu Gly Tyr Phe Gly Ile Thr Glu Lys Lys Leu
    770                 775                 780
Lys Ala Ser Ala Thr Gly Gln Lys Thr Leu Phe Asp Phe Leu Ala Lys
785                 790                 795                 800
Lys Ser Lys
```